US012661454B2

(12) United States Patent (10) Patent No.: US 12,661,454 B2
Smith et al. (45) Date of Patent: Jun. 23, 2026

(54) AGENT DELIVERY DEVICES AND RELATED METHODS

(71) Applicant: Boston Scientific Scimed, Inc., Maple Grove, MN (US)

(72) Inventors: Paul Smith, Smithfield, RI (US); Gerald Fredrickson, Westford, MA (US); Lauren Lydecker, Millbury, MA (US); Narunn Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1221 days.

(21) Appl. No.: 17/466,166

(22) Filed: Sep. 3, 2021

(65) Prior Publication Data

US 2022/0072237 A1 Mar. 10, 2022

Related U.S. Application Data

(60) Provisional application No. 63/076,005, filed on Sep. 9, 2020.

(51) Int. Cl.
*A61M 5/31* (2006.01)
*A61M 5/19* (2006.01)
*A61M 5/315* (2006.01)

(52) U.S. Cl.
CPC .......... *A61M 5/31596* (2013.01); *A61M 5/19* (2013.01); *A61M 5/31515* (2013.01)

(58) Field of Classification Search
CPC .. A61M 3/005; A61M 5/1407; A61M 5/1408; A61M 5/2066; A61M 5/2448;
(Continued)

(56) References Cited

U.S. PATENT DOCUMENTS 5,116,315 A * 5/1992 Capozzi ................ B05B 1/3436
604/82
5,814,022 A 9/1998 Antanavich et al.
(Continued)

FOREIGN PATENT DOCUMENTS

CN 106535778 A 3/2017
EP 2058022 A1 5/2009
(Continued)

OTHER PUBLICATIONS

International Search Report and Written Opinion in International Application No. PCT/US2021/049009, mailed Dec. 3, 2021 (14 pages).

*Primary Examiner* — Bhisma Mehta
*Assistant Examiner* — Haden Matthew Ritchie
(74) *Attorney, Agent, or Firm* — Bookoff McAndrews, PLLC

(57) ABSTRACT

An agent delivery device comprises: one or more agent containers at a proximal end of the agent delivery device, wherein the one or more agent containers are configured to contain one or more fluids; an insertion section comprising a tube defining one or more lumens, the insertion section coupled to the agent containers such that the one or more fluids may flow from the agent containers to the one or more lumens and out of one or more outlets of the one or more lumens; and a distal impingement structure at the distal end of the insertion section, the distal impingement structure comprising an impingement surface arranged relative to one or more outlets to impinge the one or more fluids dispensed from the one or more outlets to cause mixing of the one or more fluids for application of the fluids at a treatment site.

15 Claims, 13 Drawing Sheets

(58) Field of Classification Search
     CPC .... A61M 5/284; A61M 5/31596; A61M 5/19;
                                                   A61M 5/31515
     See application file for complete search history.

(56)                       References Cited

U.S. PATENT DOCUMENTS

|  6,165,201  | A   | 12/2000 | Sawhney et al. |
|  6,527,749  | B1  |  3/2003 | Roby et al. |
|  6,641,553  | B1  | 11/2003 | Chee et al. |
|  7,018,357  | B2* |  3/2006 | Emmons .......... A61B 17/00491 |
|             |     |         | 604/82 |
|  8,679,882  | B2  |  3/2014 | Okano |
|  9,022,975  | B2  |  5/2015 | Goodman et al. |
|  9,962,506  | B2  |  5/2018 | Hayakawa |
| 10,449,295  | B2  | 10/2019 | Yokoyama et al. |
| 2005/0263618 | A1 | 12/2005 | Spallek et al. |
| 2006/0189944 | A1 |  8/2006 | Campbell et al. |
| 2006/0253082 | A1* | 11/2006 | McIntosh ................ A61M 5/19 |
|             |     |         | 604/82 |
| 2009/0005731 | A1 |  1/2009 | Yokoyama |
| 2013/0325059 | A1 | 12/2013 | O'Neill |
| 2014/0076308 | A1 |  3/2014 | Dunne |

FOREIGN PATENT DOCUMENTS

| GB | 2120958    | A  | 12/1983 |
| JP | 2008544784 | A  | 12/2008 |
| WO | 9219383    | A1 | 11/1992 |
| WO | 2007000330 | A2 |  1/2007 |
| WO | 2009081199 | A1 |  7/2009 |
| WO | 2018234524 | A1 | 12/2018 |
| WO | 2020120498 |    |  6/2020 |

* cited by examiner

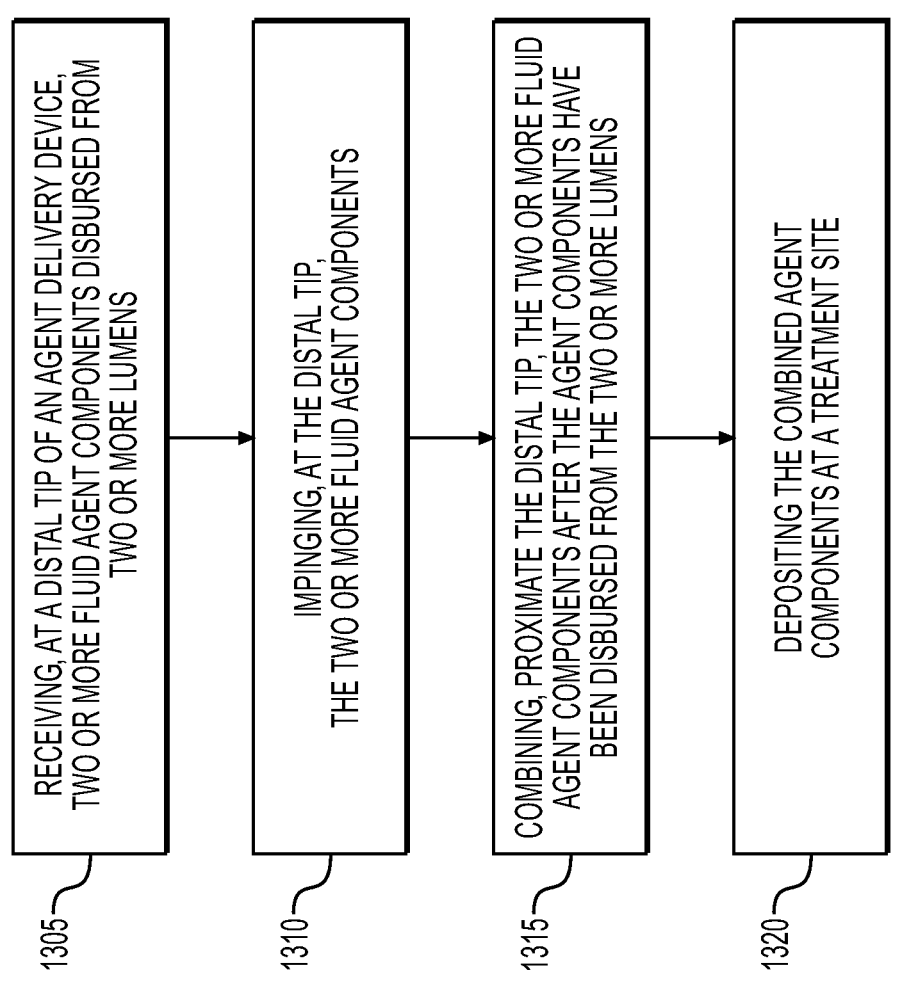

1305 — RECEIVING, AT A DISTAL TIP OF AN AGENT DELIVERY DEVICE, TWO OR MORE FLUID AGENT COMPONENTS DISBURSED FROM TWO OR MORE LUMENS

1310 — IMPINGING, AT THE DISTAL TIP, THE TWO OR MORE FLUID AGENT COMPONENTS

1315 — COMBINING, PROXIMATE THE DISTAL TIP, THE TWO OR MORE FLUID AGENT COMPONENTS AFTER THE AGENT COMPONENTS HAVE BEEN DISBURSED FROM THE TWO OR MORE LUMENS

1320 — DEPOSITING THE COMBINED AGENT COMPONENTS AT A TREATMENT SITE

*FIG. 13*

AGENT DELIVERY DEVICES AND RELATED METHODS

CROSS-REFERENCE TO RELATED APPLICATIONS

This patent application claims the benefit of priority under 35 U.S.C. § 119 to U.S. Provisional Patent Application No. 63/076,005, filed Sep. 9, 2020, which is incorporated herein by reference in its entirety.

TECHNICAL FIELD

Various aspects of the disclosure relate generally to agent delivery systems, devices, and related methods. Examples of the disclosure relate to systems, devices, and related methods for delivering an agent, such as a prophylactic, to a treatment site, for example, a tissue defect.

BACKGROUND

There exists a need to deliver agents during a treatment/ operation, and/or preoperatively and postoperatively, to target treatment sites within the body to protect those sites from tissue degradation, especially during or after endoscopic and open surgical procedures of the gastrointestinal (GI) tract. Examples of endoscopic and open surgical procedures of the GI tract include colonic resection, bariatric surgery, esoph-agectomy, gastric bypass, and sleeve gastrectomy, among others. Procedures may result in perforation, post-surgical leaks, or other wounds of the tract. It is with all of the above considerations in mind that the improvements of the present disclosure may be useful.

SUMMARY

Aspects of the disclosure relate to, among other things, systems, devices, and methods for delivering an agent, including an agent having multiple parts/components, to a target treatment site. Each of the aspects disclosed herein may include one or more of the features described in connection with any of the other disclosed aspects.

According to certain aspects of the disclosure, an agent delivery device comprises: one or more agent containers at a proximal end of the agent delivery device, wherein the one or more agent containers are configured to contain one or more fluids; an insertion section connected to the proximal end of the one or more agent containers, the insertion section comprising a tube defining one or more lumens, the insertion section coupled to the agent containers such that the one or more fluids may flow from the agent containers to the one or more lumens and out of one or more outlets of the one or more lumens; and a distal impingement structure at the distal end of the insertion section, the distal impingement structure comprising an impingement surface arranged relative to one or more outlets to impinge the one or more fluids dispensed from the one or more outlets to cause mixing of the one or more fluids for application of the fluids at a treatment site.

The agent delivery device may include one or more of the following features. The one or more agent containers may comprise two syringes, the one or more lumens may comprise two lumens, and each syringe is in fluid communication with a respective lumen of the two lumens, and actuation of the two syringes causes the one or more fluids to flow through the two lumens. The agent delivery device may further comprise a connector element fixing the two syringes to the insertion section, and wherein the tube is flexible. The one or more lumens may comprise two lumens each extending distally from a distal face of the tube, wherein longitu-dinal axes of the two lumens intersect in a manner that causes mixing of the one or more fluids dispensed from the outlets prior to the one or more fluids contacting the impingement surface. The one or more fluids may include two different components of an agent. The distal impinge-ment structure may comprise a J-shaped wire. The tube may have a diameter of less than 3.8 mm.

The agent delivery device may also include one or more of the following features. The distal impingement structure of the agent delivery device may further comprise a bottom surface connecting the distal end of the tube to the impinge-ment surface. The impingement surface and a longitudinal axis of each of the one or more lumens may form an angle between 45 degrees and 160 degrees. The distal impinge-ment structure may comprise a top surface extending distally from the impingement surface, wherein the top surface is substantially parallel to the bottom surface; and a distally-facing surface extending from the top surface and substan-tially parallel to the impingement surface. The agent deliv-ery device may further comprise a distally-facing surface extending from an edge of the impingement surface opposite from the bottom surface, wherein the distally-facing surface is substantially perpendicular to a plane of the bottom surface. The bottom surface may also comprise one or more cylindrical rods extending in a direction substantially par-allel to a longitudinal axis of the one or more lumens. The one or more fluids dispensed from the one or more outlets may form a fluid flow over the impingement surface and the top surface.

According to another aspect of the disclosure, an agent delivery device comprises: one or more agent containers at a proximal end of the agent delivery device, wherein the one or more agent containers contain one or more fluids; a flexible insertion tube connected to the proximal end of the one or more agent containers, the insertion tube defining at least one delivery lumen and a second lumen, the insertion tube coupled to the agent containers such that the one or more fluids may flow from the agent containers to the at least one delivery lumen and out of one or more outlets of the at least one delivery lumen; and a first impingement wire, wherein a proximal end of the first impingement wire is mounted in the distal end of the second lumen, the first impingement wire defining an impingement surface at a distal end of the first impingement wire, the impingement surface positioned relative to the at least one delivery lumen to impinge the one or more fluids dispensed from the one or more outlets.

The agent delivery device may include one or more of the following features. The impingement surface may be trans-verse to a longitudinal axis of the at least one delivery lumen. The agent containers comprise two containers, and the at least one delivery lumen may comprise a pair of lumens each arranged in fluid communication with a respec-tive one of the agent containers. The agent delivery device may include a second impingement wire, wherein the proxi-mal end of the second impingement wire may be mounted in a distal end of a third lumen, wherein the second impinge-ment wire may include a second impingement surface arranged on the distal end of the second impingement wire and positioned relative to one of the pair of lumens to impinge the one or more fluids dispensed from the one or more outlets.

According to another aspect of the disclosure, a method for delivering an agent to a treatment site comprises: receiv-ing, at a distal tip of an agent delivery device, two or more fluid agent components disbursed from two or more lumens; impinging, at the distal tip, the two or more fluid agent components; combining, proximate the distal tip, the two or more fluid agent components after the agent components are disbursed from the two or more lumens; and depositing the combined agent components a treatment site.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated herein and constitute a part of this specification, illustrate exemplary aspects of the disclosure and, together with the description, explain the principles of the disclosure.

FIG. 13 depicts a flowchart illustrating an exemplary method of delivering an agent to a treatment site, according to aspects of this disclosure.

DETAILED DESCRIPTION

Figure 1:
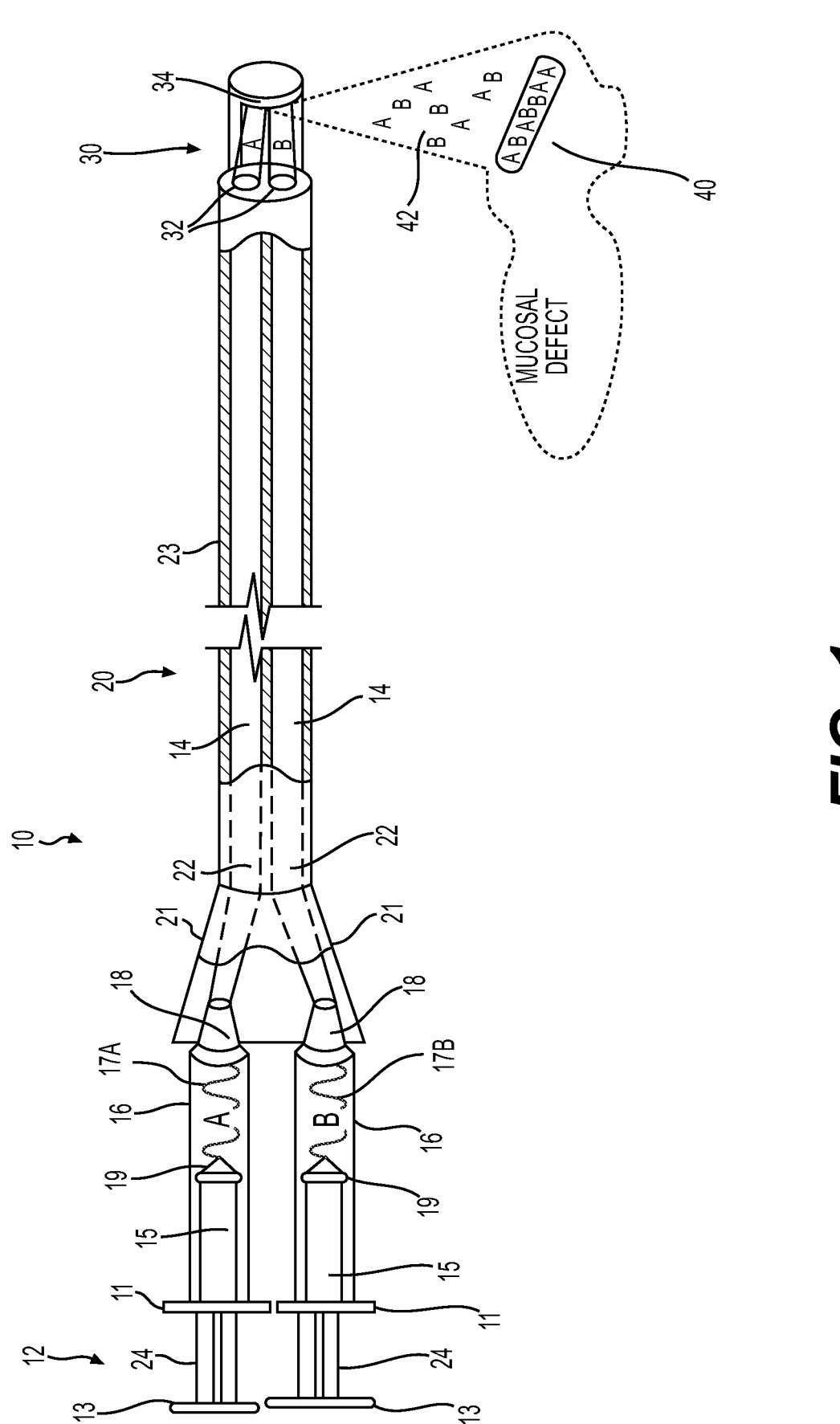
FIGS. 1 and 2 are perspective views of an exemplary medical device including a proximal end, a flexible insertion section, and a distal end including a distal impingement structure, according to aspects of this disclosure.

Aspects of this disclosure relate to application of a multi-part agent at a target tissue site, for example, to protect those sites from further tissue degradation. Some prophylactic agents include multiple parts to effectively adhere to the target tissue site. Current devices and methods for delivery of such multi-part agents are limited. With the lack of effective treatment option and tools, there is a need to apply agents to target treatment sites to protect those sites from further tissue degradation. Some agents—for example, certain prophylactic agents—may require multiple parts to be able to cure or stay adhered to a target tissue. Many agents that are delivered may also potentially cure in the catheter unless a secondary means of curing is implemented, such as photosensitive cure (i.e. light cure). Catheters for delivering agents may also have significant clogging issues due to agents curing with in them.

Aspects of the disclosure include devices and methods for delivering agents to a target tissue site within a subject (e.g., patient). Examples of the disclosure further include devices and methods for adhering a multi-part agent to a target tissue site. In some aspects, delivery includes mixing and applying a two-part agent at a target tissue site using a distal impingement structure. Delivery and placement of the agent may be via a catheter, scope (endoscope, bronchoscope, colonoscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Delivery and placement also can be in other body lumens or organs reachable via the GI tract, any other natural opening or body tract, or bodily incision.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices. Reference will now be made in detail to examples of the disclosure described above and illustrated in the accompanying drawings. Wherever possible, the same reference numbers will be used throughout the drawings to refer to the same or like parts.

Figure 2:
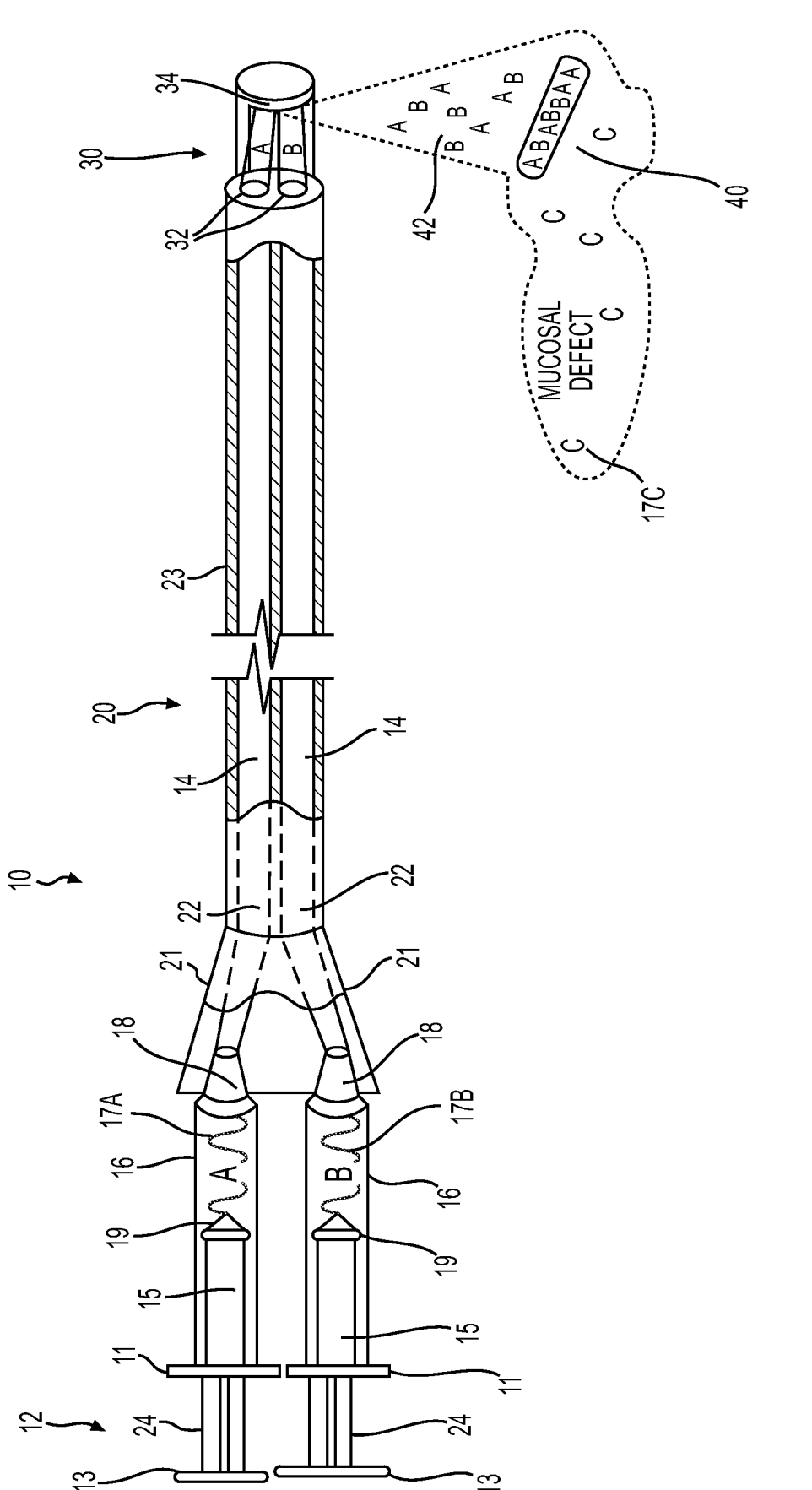

FIGS. 1 and 2 show a medical device 10 (e.g. agent delivery device) in accordance with an example of this disclosure. Medical device 10 includes a proximal end 12, a flexible insertion section 20, and a distal end 30. Proximal end 12 may include one or more agent containers, for example, syringes 24, wherein each syringe comprises a plunger flange 13, a barrel flange 11, a barrel 16, a seal 19, and a nozzle 18. Each of the one or more agent containers contains an agent component 17A, 17B that is dispersible out of the nozzle 18 and into the flexible insertion section 20. While syringes are disclosed as exemplary with respect to this embodiment, other agent containers with similar structures for containing and delivering agent components upon activation by a user are also contemplated as within the scope of this disclosure. In some embodiments, the agent component is one of two parts of a prophylactic agent, where each syringe 24 contains one of each part of the prophylactic agent. Although agent components 17A, 17B may be separate, individual compositions, in some embodiments, agent components 17A, 17B may be the same agent component.

Further, fewer or additional agent components may be incorporated in the medical device 10, e.g., to have agent components 17C, 17D, etc.

Flexible insertion section 20 comprises a flexible tube 23, lumens 14 contained within the flexible insertion section 20 for transporting agent components 17A, 17B from a proximal end to a distal end of the flexible insertion section, and connectors 21 between the nozzles 18 and lumens 14 for maintaining fluid communication between the nozzles 18 and lumens 14. The connector 21 may be configured to be fixed to the distal end of syringes 24 (agent containers) and the proximal end of flexible tube 23, by, for example, an adhesive, a heat shrink, a snap-fit connection, a threaded coupling, a crimping connection, and the like. The lumens 14 may extend through the flexible tube 23 from the proximal end in fluid communication with nozzles 18 and a distal end of the flexible tube. While lumens are discussed throughout this disclosure, the flexible insertion section 20 may comprise any separate flexible chamber, such as independent catheters, needles, cannula, co-extrusion, and/or two or more lumen extrusions for transporting agent components. In some embodiments, at least two agent components are transported through the flexible insertion section 20. In additional embodiments, the flexible insertion section 20 is of sufficient length to transport the agent components from the proximal end of the medical device, outside of the body, to a treatment site within the body during endoscopic procedures. The flexible insertion section 20 may be inserted into a GI tract via a natural orifice. The orifice can be, for example, the nose, mouth, or anus, and the placement can be in any portion of the GI tract, including the esophagus, stomach, duodenum, large intestine, or small intestine. Delivery and placement also can be in other body lumens or organs reachable via the GI tract, any other natural opening or body tract, or bodily incision.

Still referring to FIGS. 1 and 2, at the distal tip end of the medical device 10 is a distal impingement structure 34. The distal impingement structure 34 may comprise outlets 32 which are in fluid communication with the lumens 14. The proximal end of the distal impingement structure 34 may be configured to be fixed to the distal end of flexible tube 23, by, for example, an adhesive, a heat shrink, a snap-fit connection, a threaded coupling, a crimping connection, and the like. In some embodiments, the distal impingement structure may be connected to or an integral part of the lumens 14, examples of which are provided in FIGS. 10-12, discussed further below.

Upon activation of the plungers 15 of syringes 24, the seals 19 cause agent components 17A, 17B to dispense from nozzles 18 into the inlets 22 of lumens 14. The syringes 24 may be actuated to dispense agent components 17A, 17B simultaneously and/or in succession. While syringes are discussed here, any agent container for holding and delivering agent components to lumens 14 are contemplated within this disclosure. The agent components 17A, 17B subsequently flow out of the lumens 14 via outlets 32. The flow of the agent components 17A, 17B then contacts a distal impingement structure 34. The flow of the agent components 17A, 17B and the structure of the distal impingement structure 34 causes the agent components to mix in the environment (for example, air), and the combined agent 42 is deposited at a treatment site 40. In some embodiments, one or more additional lumens may be used to apply a compressed gas, liquid, or other agents to the surface. In some embodiments, a third lumen for carrying a compressed gas may be used, where the compressed gas could extend to the distal tip to add further velocity to the exiting parts of the agent components 17A, 17B. In some embodiments, the distal impingement structure 34 may be adapted to mix the agent parts including by merging distal lumens by angulation while having a thin wall of separation at the distal tip, whereas the two streams merge in air outside of the catheter. The adaptation additionally could include interrupters to further mix, mist, and/or atomize the agents.

The treatment site 40 may be, for example, a target tissue such as an ulcer, fistula, or mucosal, submucosal, or full thickness defect. In some embodiments, as shown in FIG. 2, a third agent component 17C may be pre-applied to the treatment site, such that depositing the combined agent on the treatment site as explained above results in faster or more efficient curing or additional prophylactic effects. In additional embodiments, prior to applying agent component 17C, the treatment site 40 may be flushed of contaminants such as organics or chemical residue from other treatment means (such as lifting agents, dyes, mucosal slime, blood, and compromised tissue). To prepare the surface, one of lumens 14 or an additional lumen, or device, may be extended to the target site and adapted to prepare the mucosa, submucosa, or muscle layer. The additional lumen may include a nozzle, jet needle, and/or atomizer tip, and may emit a mist.

Agent components 17A, 17B may be any agent or component thereof that is applied to a tissue site in the body. For example, agent components 17A, 17B may form cohesive and bio adhesive substrates that provide a protective covering in the GI tract. Examples of agent components for this purpose may include polysaccharides (e.g. chitosan, cellulose, alginates, etc.), poly(ethylene oxide) ("PEO"), poly (ethylene glycol) ("PEG"), and Dextran. As another example, agent components 17A, 17B may provide a protective covering or seal for a perforation, sutures, clipped tissue, and the like. Examples of agent components for this purpose may include polyamidoamine ("PAMAM"), polylysine, oxidized polysaccharides, and polyurethanes.

Figures 3, 4:
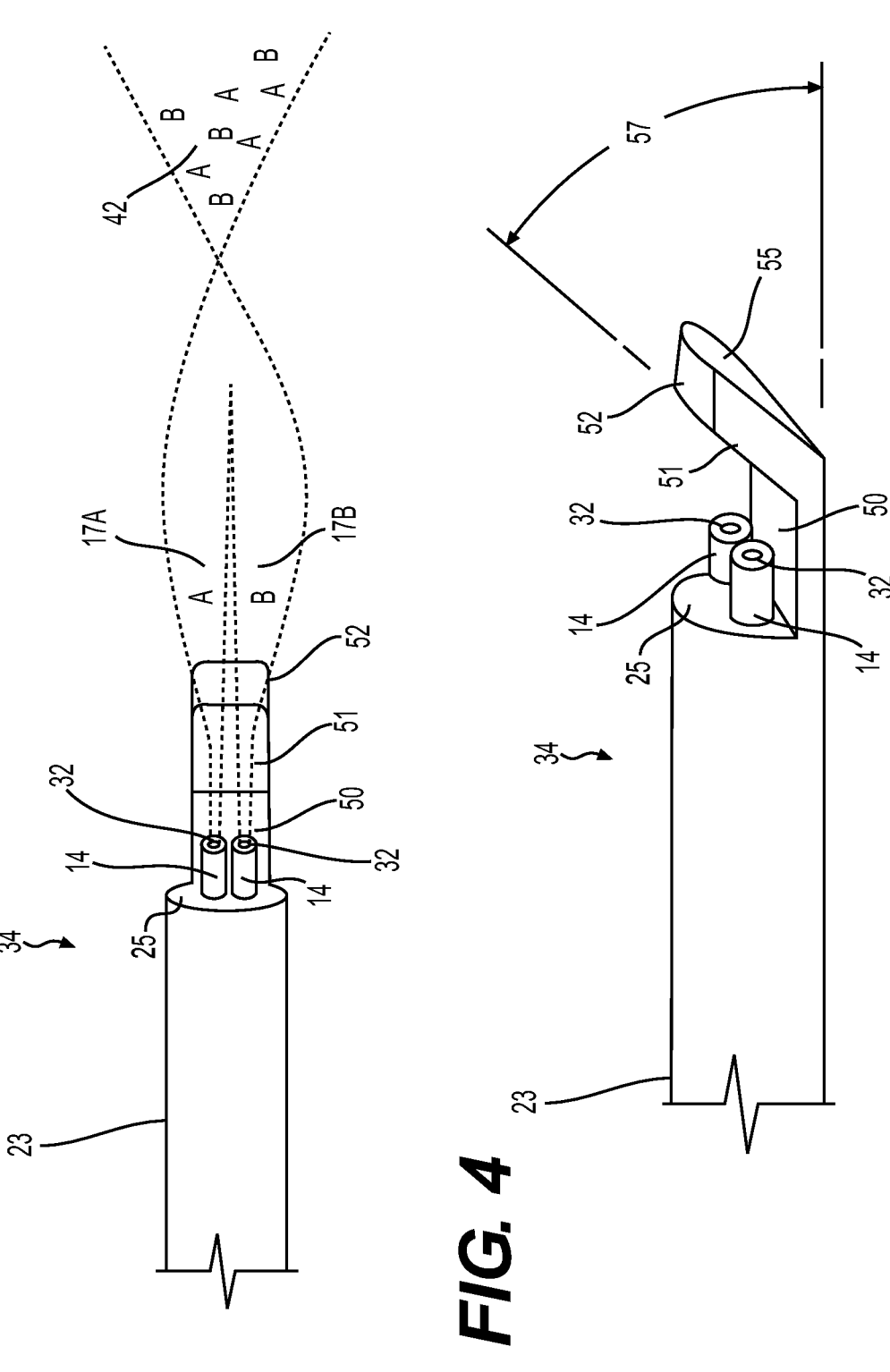
FIG. 3 is a top view of a distal impingement structure, according to aspects of this disclosure.
FIG. 4 is a side view of the distal impingement structure of FIG. 3, according to aspects of this disclosure.

FIG. 3 is a top view of the distal impingement structure 34 located at a distal tip of a medical device, like the device shown in FIG. 1. In some embodiments, the distal impingement structure 34 comprises a bottom surface 50, an impingement surface 51 facing a distal face 25 of flexible tube 23, and a top surface 52. The lumens 14 carry agent components 17A, 17B through the flexible tube 23. The lumens 14 include outlets 32 in a distal face 25 of the flexible tube 23 for dispensing agent components 17A, 17B. Distal face 25 as shown in FIG. 3 is a flat, distally-facing, partial cross-section of the flexible tube 23, but may be any suitable shape. Distal face 25 is configured to allow lumens, nozzles, outlets, or other similar structures to pass through in order for agent components to be delivered to the distal impingement structure 34. The bottom surface 50 is rectangular in shape as shown in FIG. 3, but may comprise any other suitable shapes or dimensions. The impingement surface 51 may be rectangular in shape with chamfered or curved edges as shown in FIG. 3, or may comprise any other suitable shape for impinging the flow of agent components 17A, 17B. For example, a scallop cut or valley shaped impingement surface 51 generates a narrow spray plume, which further may be beneficial for directing the spray direction. The top surface 52 may be flat or curved and partially cylindrical as shown in FIG. 3, or may comprise any suitable shape. In some embodiments, agent component 17A, 17B is dispensed from the outlets 32 with sufficient velocity such that portions of agent component 17A, 17B form one or more streams over the bottom surface 50, impingement surface 51, and/or top surface 52. In some embodiments, a substantial portion of agent component 17A, 17B contacts only impingement surface 51 before application to the treatment site. In other embodiments, portions of agent component 17A, 17B flow across bottom surface 50, impingement surface 51, and top surface 52. The lumens 14, outlets 32, bottom surface 50, impingement surface 51, and top surface 52 are configured such that agent components 17A, 17B mix together to create a combined agent 42 applied to the treatment site. The distal impingement structure 34 of this embodiment causes significant increase in mixing after the streams contact the impingement surface 51. For example, as further shown in FIG. 3, two distinct flows for agent components 17A, 17B exit the outlets 32 and contact impingement surface 51. After contact, the streams are directed radially and distally, e.g. the streams have two velocity components, a first velocity component distally toward the target treatment site and a second velocity component radially away from the axis of lumens 14. As the stream gets further away from the impingement structure, redirection and dissipation of energy causes the streams to spread. In addition to mixing the streams, as the streams spread, elements of agent component 17A, 17B mix together in the center, resulting in a convergence and mixing of the streams and ultimately a combined agent 42 applied to the treatment site.

FIG. 4 is a side view of the distal impingement structure 34 of FIG. 3. The distal impingement structure 34 may comprise a bottom surface 50, an impingement surface 51 facing a distal face 25 of flexible tube 23, a top surface 52, an outer surface 55, and an impingement surface angle 57. Similar to FIG. 3, distal face 25 may be a flat, partial cross-section of the flexible tube 23 that is configured to allow lumens, nozzles, outlets, or other similar structures to pass through in order for agent components to be delivered to the distal impingement structure 34. The bottom surface 50 may be substantially flat and rectangular in shape as shown in FIG. 4, but may comprise any other suitable shapes or dimensions. The impingement surface 51 may be rectangular in shape with chamfered or curved edges as shown in FIG. 4, or may comprise any other suitable shape for impinging the flow of agent components 17A, 17B. The top surface 52 may be partially cylindrical as shown in FIG. 4, or may comprise any suitable shape. In some embodiments, the outer surface 55 may be parallel to the impingement surface 51. Impingement surface 51 comprises an impingement surface angle 57, where the impingement surface angle is the angle of the impingement surface relative to the plane defined by the bottom surface 50 of the distal impingement structure 34. In some embodiments, the impingement surface angle may be the angle of the impingement surface 51 relative to longitudinal axes of lumens 14 taken at or near outlets 32. Impingement surface angle 57 may be configured so that the flow of agent component 17A, 17B impinges on impingement surface 51 and combines the components 17A,

17B into a combined agent 42 that is applied to the target tissue. In some embodiments, the impingement surface angle 57 may be between 45 degrees and 160 degrees. In additional embodiments, the flexible tube diameter is less than 3.8 mm. In further embodiments, the distance between the outlets 32 and the impingement surface 51 is less than 3 mm. In other embodiments, the distance from distal face 25 to the closest portion of top surface 52 is less than 3 mm. In some embodiments, the distance between the centers of each of outlets 32 may be between 0.1 and 3.8 mm.

Figure 5:
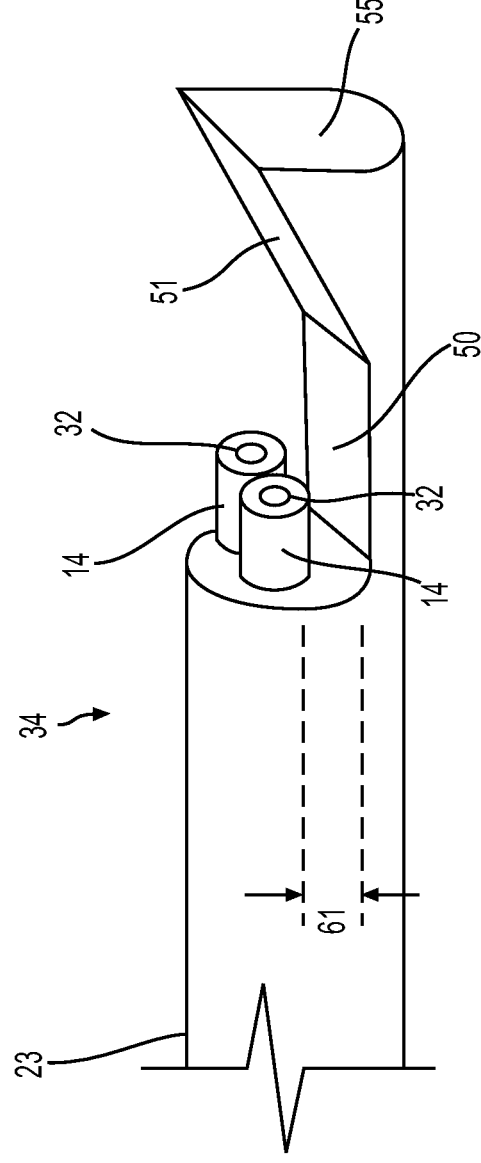
FIG. 5 is a side view of another exemplary embodiment of a distal impingement structure featuring an outlet height, according to aspects of this disclosure.

FIG. 5 is a side view of an alternate embodiment of the distal impingement structure 34 for use with a medical device like that shown in FIG. 1. The distal impingement structure 34 may comprise a distal end of a flexible tube 23, lumens 14, outlets 32, a bottom surface 50, an impingement surface 51, an outer surface 55, and an outlet height 61. The outlet height 61 may be the distance from the plane of the bottom surface 50 to the lumens 14 and/or outlet 32. In some embodiments, the outlet height 61 is the approximate distance between the bottom surface 50 and the bottom of the outlets 32. The outlet height 61 is configured to reduce residual puddling of materials on the bottom surface 50 which may be caused by surface tension. In some embodiments, the outlet height is selected in order to reduce the portion of agent component 17A, 17B that contacts bottom surface 50 while increasing the portion of agent component 17A, 17B that contacts the impingement surface 51. In some embodiments, the outlet height is between 0.025 mm and 3.8 mm.

Figure 6:
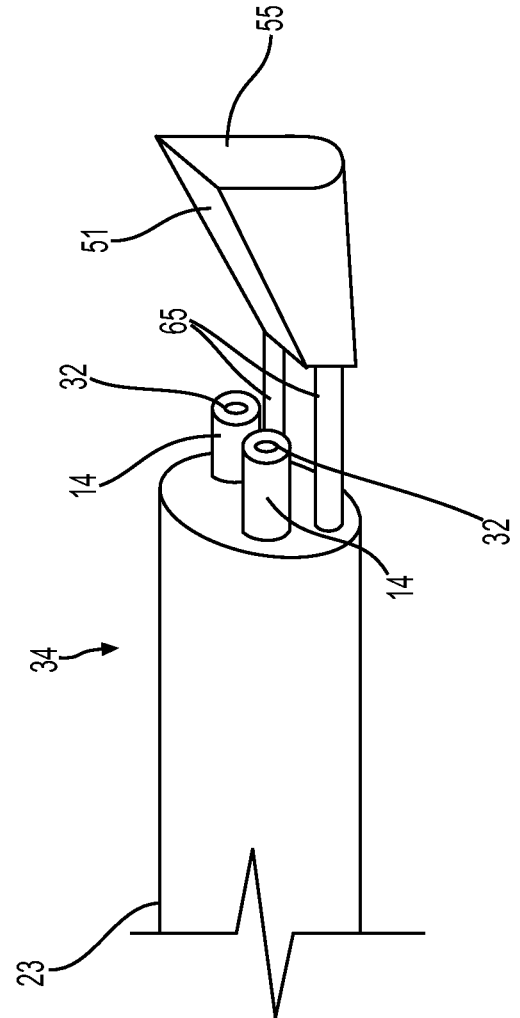
FIG. 6 is a side view of a further exemplary embodiment of a distal impingement structure including a bottom surface consisting of cylindrical rods, according to aspects of this disclosure.

FIG. 6 is a side view of an alternate embodiment of a distal impingement structure 34 for use in a medical device like the one shown in FIG. 1. The distal impingement structure 34 may comprise an impingement surface 51 facing a distal face 25 of flexible tube 23, an outer surface 55, and cylindrical rods 65. The cylindrical rods 65 may connect the flexible tube 23 to the impingement surface 51, and are configured to allow a portion of agent component 17A, 17B to flow between or around the cylindrical rods 65. In some embodiments, the outlets 32 are located directly above the gap in between the cylindrical rods 65, to reduce residual puddling of fluids on the cylindrical rods that may be caused by surface tension. In some embodiments, the cylindrical rods 65 may be parallel to each other and/or parallel to lumens 14. The cylindrical rods 65 may further be rigid. The cylindrical rods 65 may also extend further from the distal face 25 than lumens 14 extends from distal face 25. In some embodiments, cylindrical rods 65 may comprise a total of two cylindrical rods as shown in FIG. 6. The cylindrical rods may further have a round cross-section.

Figure 7:
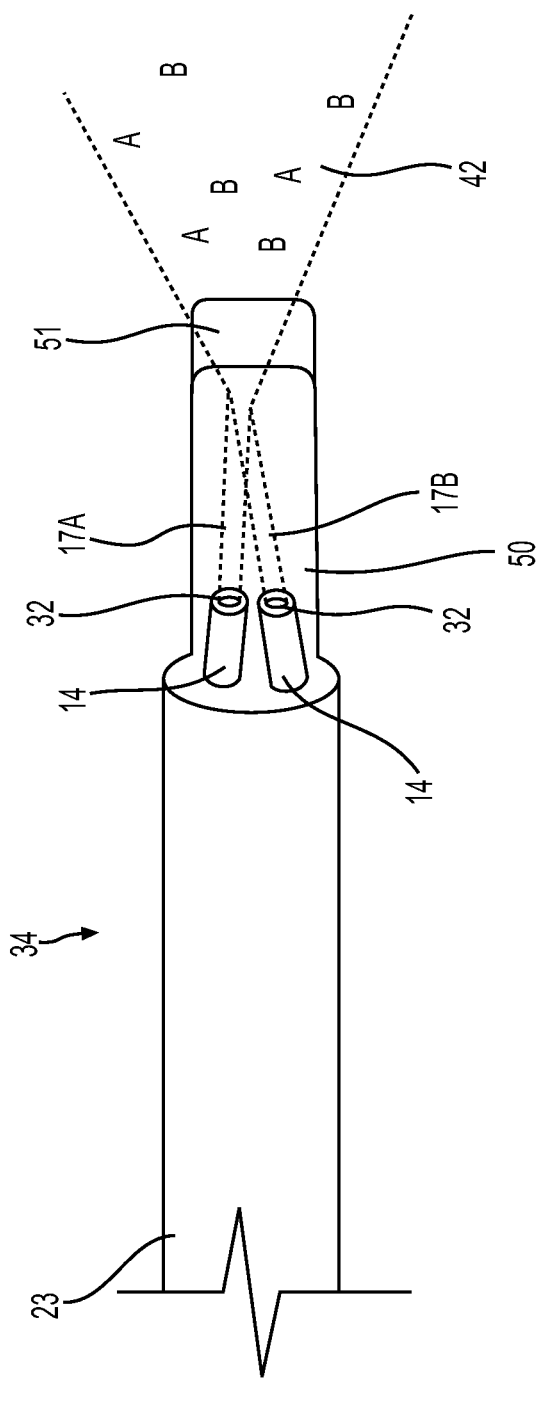
FIG. 7 is a top view of another exemplary embodiment of the distal impingement structure including lumens having intersecting axes, according to aspects of this disclosure.

FIG. 7 is a top view of an exemplary embodiment of another distal impingement structure 34 that may be used with a medical device like the one shown in FIG. 1. The distal impingement structure 34 may comprise a flexible tube 23, lumens 14, outlets 32, a bottom surface 50, and an impingement surface 51. The lumens 14 may further having intersecting longitudinal axes. The axes may interest at or near the impingement surface 51. The lumens 14 are configured to promote mixing of agent components 17A, 17B as the agent is dispersed from the outlets 32 of lumens 14, resulting in application of combined agent 42 to the treatment site. In some embodiments, the lumens are configured such that the streams do not substantially contact each other prior to contacting the impingement surface 51.

Figure 8:
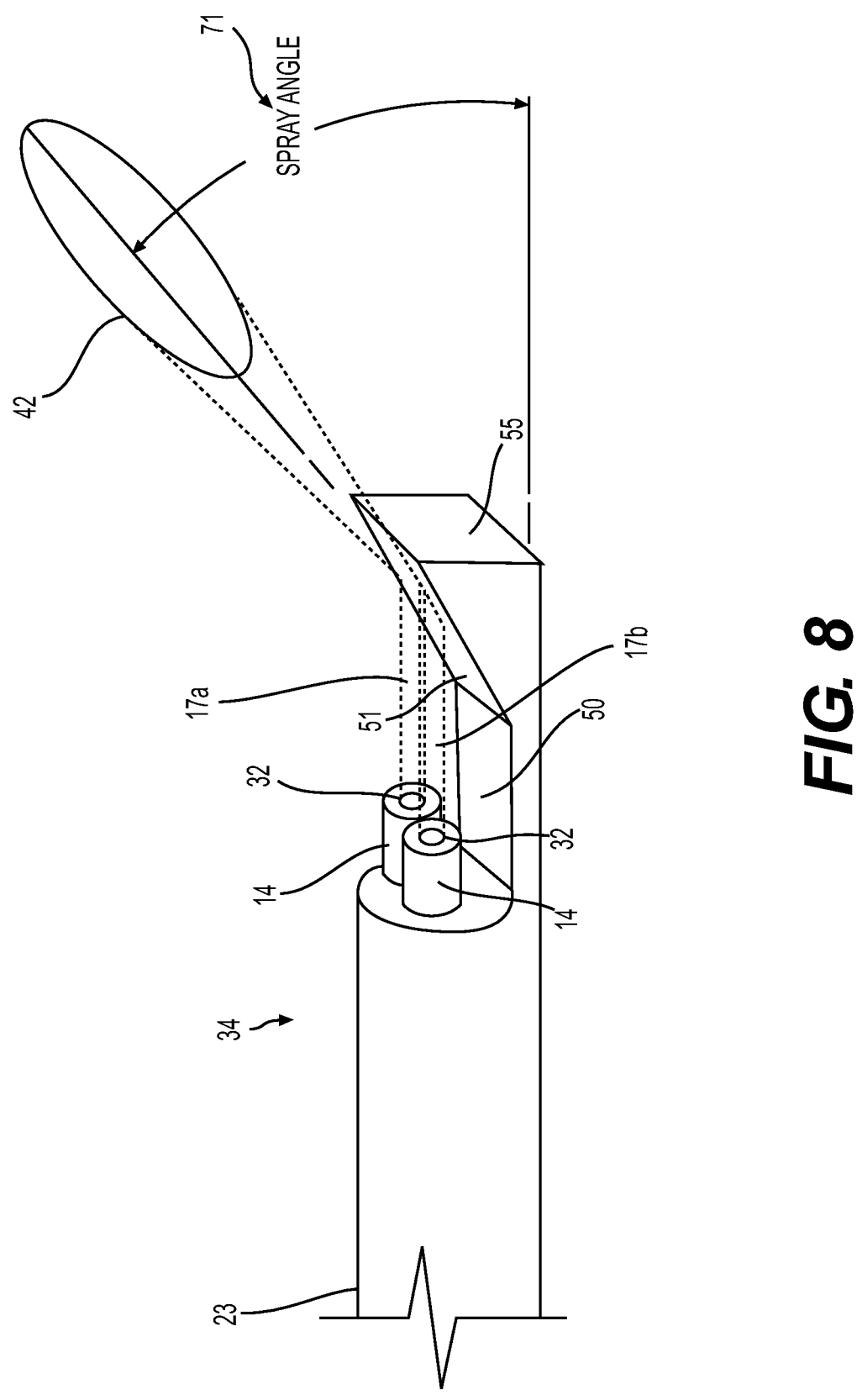
FIG. 8 is a side view of an exemplary embodiment of a distal impingement structure including a spray angle, according to aspects of this disclosure.

FIG. 8 is a side view of an exemplary embodiment of a distal impingement structure 34 for use with a medical device like the one shown in FIG. 1. The distal impingement structure 34 may comprise a distal end of flexible tube 23, lumens 14, outlets 32, bottom surface 50, impingement surface 51, and outer surface 55, and may further be configured to generate a spray angle 71. Spray angle 71 is the angle at which a portion of agent component 17A, 17B flows relative to the plane of the bottom surface 50 (in this case, that plane being parallel to a longitudinal axis of each lumens 14 at or near the outlets 32). In some embodiments, the spray angle 71 is the angle at which a substantial or majority portion of agent component 17A, 17B flows relative to the plane of the bottom surface 50. The spray angle 71 is at least partly dictated by the impingement surface angle 57 (shown in FIG. 4).

Figures 9A, 9B:
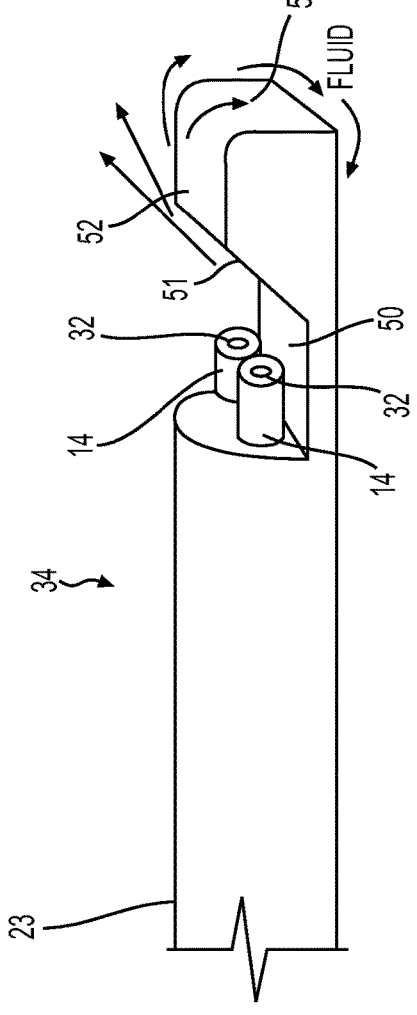
FIGS. 9A-D are side views of various implementations of a distal impingement structure, according to aspects of this disclosure.
Figure 9C:
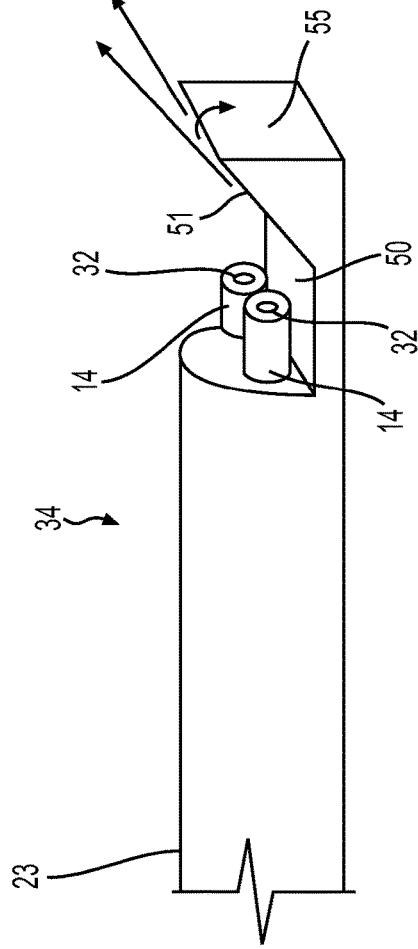
Figure 9D:
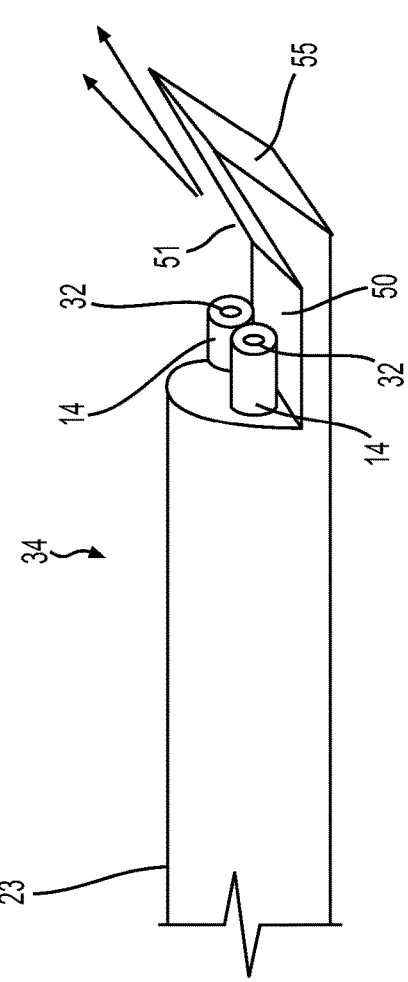

FIGS. 9A-D are side views of additional examples of distal impingement structures 34. For example, impingement surface 51, top surface 52, and outer surface 55 may be configured as shown in FIG. 9A. As further shown in FIG. 9A, the top surface 52 and outer surface 55 may be filleted or chamfered, having a rounded top edge, to facilitate flow of a portion of agent component 17A, 17B over the impingement surface 51, top surface 52, and outer surface 55. Top surface 52 may be flat and substantially parallel to the axes of lumens 14 and/or the bottom surface 50. This may or may not be desirable depending on the application/use. With respect to FIG. 9B, the top surface 52 and outer surface 55 may be configured such that the outer surface 55 is substantially parallel to the impingement surface 51 (and therefore faces distally and radially outward), resulting in a reduction in flow of agent component 17A, 17B around the outer surface 55. The top surface 52 of FIG. 9B may be substantially shorter than the top surface of 9A, and further, there may be no chamfering between top surface 52 and outer surface 55 such that there is a defined edge between the two surfaces. With respect to FIG. 9C, the impingement surface 51 may be configured to directly interface with the outer surface 55, e.g. not including a top surface 52. Instead, impingement surface 51 and outer surface 55 meet at an edge that is transverse (e.g. perpendicular to) the axes of lumens 14. In addition, the outer surface 55 in FIG. 9C is substantially perpendicular to the plane of the bottom surface 50 and the axes of lumens 14, which further reduces the flow of agent component 17A, 17B over the outer surface 55. In yet another embodiment reflected in FIG. 9D, the impingement surface 51 and the outer surface 55 may be configured at different angles relative to the plane of the bottom surface 50 (and or axes of lumens 14), such that the flow of agent component 17A, 17B over the outer surface 55 is eliminated or nearly eliminated. For example, the top surface 52 may be omitted, and impingement surface 51 and the outer surface 55 may meet at an edge. The edge between impingement surface 51 and outer surface 55 is transverse to (and in some embodiments, perpendicular to) axes of lumens 14. The angle of impingement surface 51 relative to the bottom surface 50 and the longitudinal axes of lumens 14 may be greater than the angle of outer surface 55 relative to bottom surface 50 and the longitudinal axes of lumens 14. Outer surface 55 may further face distally and radially outward.

Figure 10:
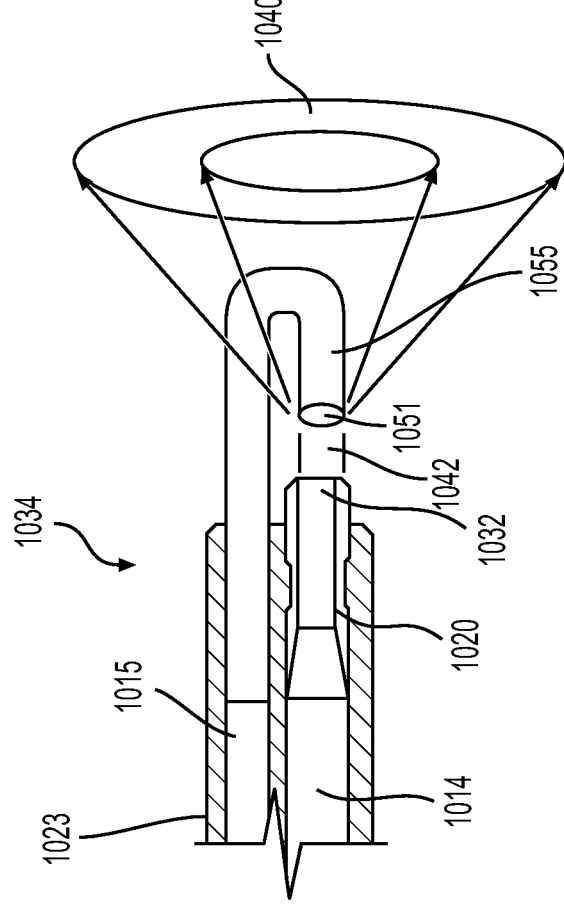
FIG. 10 is a perspective view of an exemplary embodiment of a distal impingement structure comprising an impingement wire with an impingement surface parallel to the outlet, according to aspects of this disclosure.

FIG. 10 depicts a perspective, partial cross-sectional view of another exemplary distal impingement structure in accordance with an example of this disclosure. The distal impingement structure 1034 comprises a nozzle 1020, a flexible tube 1023, an outlet 1032, an impingement surface 1051, and an impingement wire 1055. Lumen 1014 is configured to deliver a combined agent 1042 through flexible tube 1023 and disburses the combined agent 1042 via an outlet 1032 of a nozzle 1020 fixed in the distal end of the lumen 1014. Lumen 1014 may comprise any chamber within a catheter, needle, cannula, co-extrusion, and/or two or more lumen extrusion for transporting agent components. A source of combined agent 1042 may be proximal of lumen 1014. That source could be any suitable source of delivering such agent, including elements of embodiments shown in FIGS. 1-9B, such as a multi-lumen catheter carrying agent components 17A, 17B, and syringes (or other agent containers) for providing agent components 17A, 17B. Lumen 1015 is configured to hold, at its distal end, the proximal end of impingement wire 1055. In some embodiments, the impingement wire 1055 is mounted or affixed in the distal end of lumen 1015. The impingement wire 1055 may be a J-shaped wire with a circular cross-sectional shape as shown in FIG. 10, or may have other shapes (U-shaped, L-shaped, etc.) and/or cross-sectional shapes (oval, square, rectangular, and so forth). The impingement wire 1055 also comprises an impingement surface 1051. The impingement surface 1051 may be configured to match the size and shape of outlet 1032, or may be configured to be larger or smaller in diameter than outlet 1032. In some embodiments, the impingement surface 1051 may also be positioned to align with outlet 1032. Combined agent 1042 disbursed at the outlet 1032 impinges surface 1051 for application of the combined agent 1042 to the treatment surface 1040. In some embodiments, the impingement surface 1051 is parallel to the plane of the outlet 1032, such that a donut (annular) shaped spray is generated for applying the combined agent 1042 to the treatment site. The impingement wire 1055 may consist of any suitable material including but not limited to metals, glass, plastics, polymers, and the like.

Figure 11:
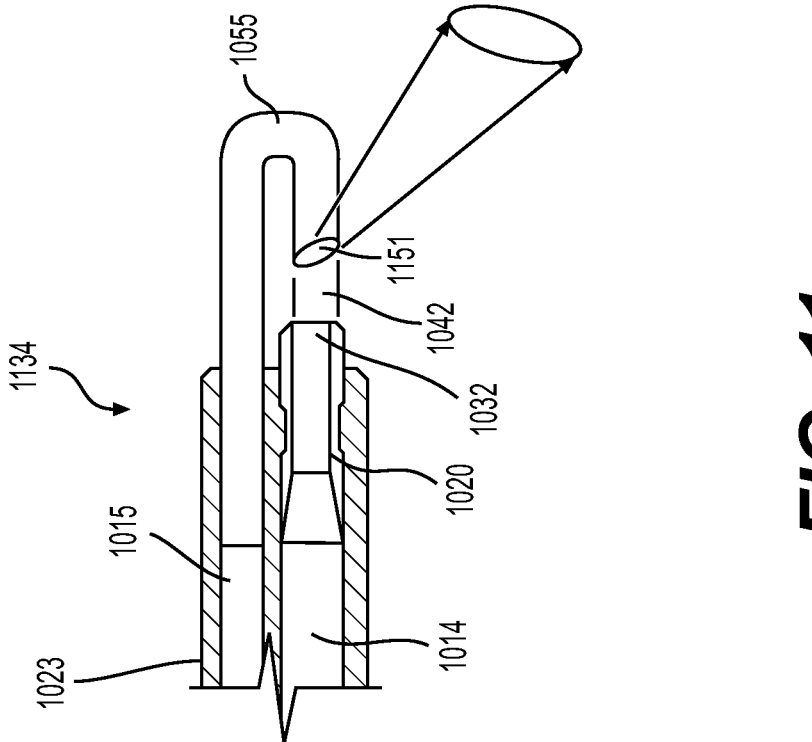
FIG. 11 is a perspective view of an exemplary embodiment of another distal impingement structure comprising an impingement wire with an impingement surface angled relative to the outlet, according to aspects of this disclosure.

FIG. 11 depicts another perspective, partial cross-sectional view of a distal impingement structure 1134 in accordance with an example of this disclosure. The distal impingement structure 1134 is identical to the distal impingement structure 1034 in FIG. 10, except the impingement surface 1151 is oval and provided at an angle relative to the plane of the outlet 1032 in order to better direct spray away from the outlet 1032, in a radial direction.

Figure 12:
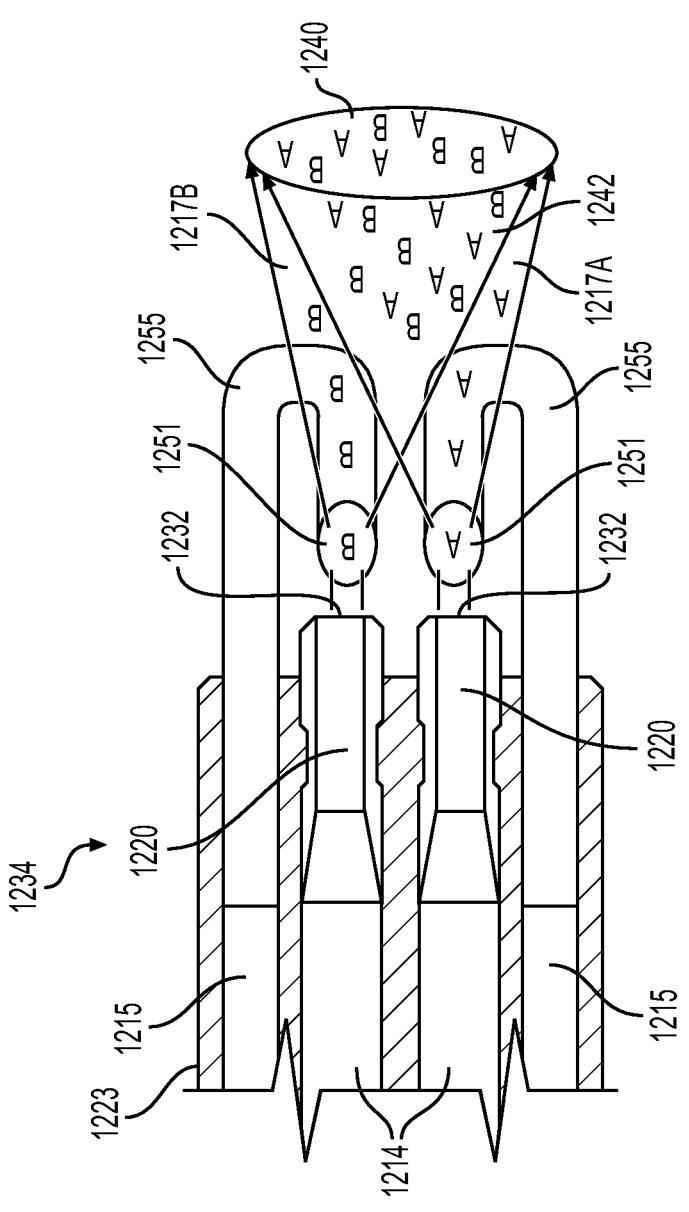
FIG. 12 is a perspective view of an exemplary embodiment of a further distal impingement structure comprising two outlets and two impingement wires with impingement surfaces facing the outlets, according to aspects of this disclosure.

FIG. 12 depicts an additional perspective, partial cross-sectional view of an exemplary embodiment of a distal impingement structure 1234. The distal impingement structure 1234 comprises nozzles 1220, outlets 1232, impingement surfaces 1251, and impingement wires 1255. Lumens 1214, comprising a pair, are configured to deliver agent components 1217A, 1217B through flexible tube 1223 and disburses the agent components 1217A, 1217B via outlets 1232 of nozzles 1220 fixed in the distal ends of the lumens 1214. Lumens 1214 may comprise any chamber within a catheter, needle, cannula, co-extrusion, and/or two or more lumen extrusion for transporting agent components. Lumens 1215 are configured to hold, at their distal ends, the proximal ends of impingement wires 1255. The impingement wires 1255 may be J-shaped with a circular cross-sectional shape as shown in FIG. 12, or may have other shapes (U-shaped, L-shaped, etc.) and/or cross-sectional shapes (oval, square, rectangular, and so forth). The impingement wire 1055 also comprises an impingement surface 1051. The impingement surface 1051 may be configured to match the size and shape of outlet 1032, or may be configured to be larger or smaller in diameter than outlet 1032. In some embodiments, the impingement surface 1051 may also be configured to align with outlet 1032. Agent components 1217A, 1217B disbursed at the outlets 1232 impinge impingement surface 1251 to facilitate mixing in air, such that a combined agent 1242 is applied to a treatment site 1240. In some embodiments, the impingement surfaces 1251 are provided at an angle relative to the plane of the outlets 1032. In some embodiments, impingement surfaces 1251 may be angled to direct agent component spray away from outlets 1232; in the case of adhesives, this reduces the possibility of clogging or obstructing flow through nozzles 1220 and outlets 1232. In some embodiments, lumens 1014, nozzles 1220, and outlets 1232 may be proximal and substantially parallel to each other to facilitate uniform mixing of streams of agent components 1217A, 1217B. In some embodiments, impingement wires 1255 may mirror each other and have identical shapes, cross-sectional shapes, and impingement surfaces 1251 for a substantial uniform circular application of materials at the treatment site 1240. In other embodiments, impingement wires 1255 may have different shapes, cross-sectional shapes, and/or impingement surfaces 1251 to achieve different application profiles at the treatment site.

FIG. 13 depicts a flowchart illustrating an exemplary method of delivering an agent to a treatment site, according to aspects of this disclosure. At step 1305, a distal tip of an agent delivery device, such as the distal tip discussed above with respect to FIGS. 1-12, receives two or more fluid agent components disbursed from two or more lumens. At step 1310, the distal tip impinges the two or more fluid agent components as discussed above with respect to FIGS. 1-2. At step 1315, proximate the distal tip, the two or more fluid agent components are combined after the agent components have been disbursed from the two or more lumens. At step 1320, the combined agent is deposited at a treatment site as discussed above with respect to FIGS. 1-12.

Each of the aforementioned systems, devices, assemblies, and methods may be used to protect and/or treat treatment sites by delivering one or more components of an agent to the treatment site. By providing a medical device with multiple lumens for delivering an agent in parts, and mixing the components after dispensing the agents from the lumens using a distal tip impingement structure, known problems associated with invasive surgical procedures and/or premature curing and clogging of catheters are avoided. Accordingly, physicians may reduce the overall procedure time, increase efficiency of procedures, and/or avoid unnecessary harm to a subject's body caused by limited ability of other tools/devices to treat perforations, post-surgical leaks, or other wounds that might result from endoscopic and open surgical procedures of the gastrointestinal (GI) tract.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only, with a true scope of the disclosure being indicated by the following claims and their equivalents.

What is claimed is:

1. An agent delivery device, comprising:
one or more agent containers at a proximal end of the agent delivery device, wherein each agent container of the one or more agent containers is configured to contain a fluid;
an insertion section connected to a distal end of the one or more agent containers, the insertion section comprising a flexible tube defining one or more lumens, the tube being configured to be inserted into a gastrointestinal tract of a subject with the proximal end of the agent delivery device remaining outside of the gastrointestinal tract, the insertion section coupled to the one or more agent containers such that the fluid of the one or more agent containers is able to flow from the one or more agent containers to the one or more lumens and out of one or more outlets of the one or more lumens; and
a distal impingement structure at the distal end of the insertion section, the distal impingement structure comprising an impingement surface and a bottom surface connecting the distal end of the tube to the impingement surface, wherein the impingement surface is arranged distal to the one or more outlets to impinge the fluid of the one or more agent containers dispensed from the one or more outlets to cause mixing of the fluid of the one or more agent containers for application of the fluid of the one or more agent containers at a treatment site,
wherein the bottom surface comprises one or more cylindrical rods extending in a direction substantially parallel to a longitudinal axis of the one or more lumens, and
wherein the one or more fluids dispensed out of the one or more outlets moves through a space extending from the one or more outlets to the impingement surface, wherein the space is radially enclosed by only the bottom surface.

2. The agent delivery device of claim 1, wherein the impingement surface and a longitudinal axis of each of the one or more lumens form an angle between 45 degrees and 160 degrees.

3. The agent delivery device of claim 2, wherein the distal impingement structure comprises:
a top surface extending distally from the impingement surface, wherein the top surface is substantially parallel to the bottom surface; and
a distally-facing surface extending from the top surface and substantially parallel to the impingement surface.

4. The agent delivery device of claim 3, wherein the fluid of the one or more agent containers dispensed from the one or more outlets form a fluid flow over the impingement surface and the top surface.

5. The agent delivery device of claim 2, further comprising a distally-facing surface extending from an edge of the impingement surface opposite from the bottom surface, wherein the distally-facing surface is substantially perpendicular to a plane of the bottom surface.

6. The agent delivery device of claim 1, wherein the one or more lumens comprise two lumens each extending distally from a distal face of the tube.

7. The agent delivery device of claim 6, wherein longitudinal axes of the two lumens intersect in a manner that causes mixing of the fluid of the one or more agent containers dispensed from the outlets prior to the fluid of the one or more agent containers contacting the impingement surface.

8. The agent delivery device of claim 1, further comprising an additional lumen within the tube and configured to deliver a compressed gas proximate the one or more outlets of the one or more lumens.

9. The agent delivery device of claim 1, wherein the one or more outlets are distalmost openings through which the one or more fluids are able to flow.

10. The agent delivery device of claim 1, wherein the distal end is at a distalmost end of the agent delivery device.

11. The agent delivery device of claim 1, wherein the one or more outlets are separated from the bottom surface by an outlet height.

12. An agent delivery device, comprising:

one or more agent containers at a proximal end of the agent delivery device, wherein the one or more agent containers contain one or more fluids;

a flexible insertion tube connected to a distal end of the one or more agent containers and configured to be inserted into a gastrointestinal tract of a subject, the insertion tube defining at least one delivery lumen and a second lumen, the insertion tube coupled to the agent containers such that the one or more fluids are able to flow from the agent containers to the at least one delivery lumen and out of one or more outlets of the at least one delivery lumen; and a first impingement wire, wherein a proximal end of the first impingement wire is mounted in a distal end of the second lumen, the first impingement wire having an impingement surface at an end of the first impingement wire, the impingement surface positioned distally of the at least one delivery lumen to impinge the one or more fluids dispensed from the one or more outlets.

13. The agent delivery device of claim 12, wherein the impingement surface is transverse to a longitudinal axis of the at least one delivery lumen.

14. The agent delivery device of claim 12, further comprising a second impingement wire, wherein the proximal end of the second impingement wire is mounted in a distal end of a third lumen, wherein the second impingement wire includes a second impingement surface on an end of the second impingement wire.

15. An agent delivery device, comprising:

one or more agent containers at a proximal end of the agent delivery device, wherein each agent container of the one or more agent containers is configured to contain a fluid;

an insertion section connected to a distal end of the one or more agent containers, the insertion section comprising a flexible tube defining one or more lumens, the tube being configured to be inserted into a gastrointestinal tract of a subject with the proximal end of the agent delivery device remaining outside of the gastrointestinal tract, the insertion section coupled to the one or more agent containers such that the fluid of the one or more agent containers is able to flow from the one or more agent containers to the one or more lumens and out of one or more outlets of the one or more lumens, wherein the tube further comprises an additional tube configured to deliver a compressed gas proximate the one or more outlets of the one or more lumens; and a distal impingement structure at the distal end of the insertion section, the distal impingement structure comprising an impingement surface and a bottom surface connecting the distal end of the tube to the impingement surface, wherein the impingement surface is arranged distal to the one or more outlets to impinge the fluid of the one or more agent containers dispensed from the one or more outlets to cause mixing of the fluid of the one or more agent containers for application of the fluid of the one or more agent containers at a treatment site, wherein the one or more fluids dispensed out of the one or more outlets moves through a space extending from the one or more outlets to the impingement surface, wherein the space is radially enclosed by only the bottom surface.

* * * * *